(12) United States Patent
MacDonald et al.

(10) Patent No.: US 8,816,234 B2
(45) Date of Patent: Aug. 26, 2014

(54) ACOUSTO-OPTIC SORTING

(75) Inventors: Michael MacDonald, Fife (GB); Kishan Dholakia, Fife (GB); Daniel Rhodes, Fife (GB); Graham Milne, Fife (GB)

(73) Assignee: The University Court of the University of St. Andrews

( * ) Notice: Subject to any disclaimer, the term of this patent is extended or adjusted under 35 U.S.C. 154(b) by 446 days.

(21) Appl. No.: 12/442,325

(22) PCT Filed: Sep. 20, 2007

(86) PCT No.: PCT/GB2007/003578
§ 371 (c)(1),
(2), (4) Date: Aug. 10, 2009

(87) PCT Pub. No.: WO2008/035083
PCT Pub. Date: Mar. 27, 2008

(65) Prior Publication Data
US 2010/0032555 A1    Feb. 11, 2010

(30) Foreign Application Priority Data

Sep. 21, 2006  (GB) .................................... 0618606.8
Jan. 15, 2007  (GB) .................................... 0700738.8

(51) Int. Cl.
*B03C 7/00* (2006.01)
*G01N 15/02* (2006.01)
*G01N 15/14* (2006.01)

(52) U.S. Cl.
CPC ...... *G01N 15/0205* (2013.01); *G01N 2015/149* (2013.01)
USPC .......................... 209/129; 435/173.1; 250/251

(58) Field of Classification Search
USPC ................ 209/129, 132; 250/251; 435/137.1, 435/173.1
See application file for complete search history.

(56) References Cited

U.S. PATENT DOCUMENTS

| | | | |
|---|---|---|---|
| 3,710,279 A | 1/1973 | Ashkin | |
| 4,523,682 A | 6/1985 | Barmatz et al. | |
| 5,158,889 A | 10/1992 | Hirako et al. | |
| 5,245,466 A * | 9/1993 | Burns et al. | 359/296 |
| 5,938,904 A | 8/1999 | Bader et al. | |
| 6,216,538 B1 | 4/2001 | Yasuda et al. | |
| 6,416,190 B1 | 7/2002 | Grier et al. | |
| 6,548,124 B1 | 4/2003 | Brumer et al. | |
| 6,833,542 B2 * | 12/2004 | Wang et al. | 250/251 |

(Continued)

FOREIGN PATENT DOCUMENTS

| | | |
|---|---|---|
| CA | 2493411 | 2/2004 |
| DE | 19952322 | 5/2001 |

(Continued)

OTHER PUBLICATIONS

Han, et al., "Separation of Long DNA Molecules in a Microfabricated Entropic Trap Array," *Science*, May 12, 2000, pp. 1026-1029, vol. 288, www.sciencemag.org.

(Continued)

*Primary Examiner* — Joseph C Rodriguez
(74) *Attorney, Agent, or Firm* — Alston & Bird LLP (57) ABSTRACT

A method for sorting particles in a fluid. The method involves generating an optical landscape using an acousto-optic device. Preferably, the optical landscape is arranged to sort particles based on size or refractive index or shape.

26 Claims, 7 Drawing Sheets

(56) References Cited

U.S. PATENT DOCUMENTS

| | | | |
|---|---|---|---|
| 6,974,927 B2* | 12/2005 | Hannah | 209/129 |
| 7,161,140 B2 | 1/2007 | Grier et al. | |
| 7,351,953 B2* | 4/2008 | Grier et al. | 250/251 |
| 7,449,679 B2* | 11/2008 | Plewa et al. | 250/251 |
| 7,612,355 B2* | 11/2009 | Wu et al. | 250/559.04 |
| 7,732,758 B2* | 6/2010 | Dholakia et al. | 250/251 |
| 8,298,727 B2* | 10/2012 | Grier | 430/1 |
| RE44,711 E* | 1/2014 | Wu et al. | 250/559.04 |
| 2002/0160470 A1* | 10/2002 | Zhang | 435/173.1 |
| 2002/0185592 A1 | 12/2002 | Grier et al. | |
| 2003/0007894 A1 | 1/2003 | Wang et al. | |
| 2003/0047676 A1 | 3/2003 | Grier et al. | |
| 2003/0111594 A1 | 6/2003 | Getin | |
| 2004/0021949 A1 | 2/2004 | Grier et al. | |
| 2004/0067167 A1* | 4/2004 | Zhang et al. | 422/82.05 |
| 2004/0089798 A1 | 5/2004 | Gruber et al. | |
| 2005/0247866 A1 | 11/2005 | Plewa | |
| 2006/0177940 A1 | 8/2006 | Furst | |
| 2009/0188795 A1* | 7/2009 | Oakey et al. | 204/451 |
| 2010/0047761 A1* | 2/2010 | MacDonald et al. | 435/2 |

FOREIGN PATENT DOCUMENTS

| | | |
|---|---|---|
| JP | 05 026799 | 2/1993 |
| WO | WO 98/10267 | 3/1998 |
| WO | WO 02/84276 | 10/2002 |
| WO | WO 03/062867 | 7/2003 |
| WO | WO 02/87792 | 11/2003 |
| WO | WO 2004/012133 | 2/2004 |
| WO | WO 2004/082840 | 9/2004 |
| WO | WO 2004/100175 | 11/2004 |
| WO | WO 2005/054818 | 6/2005 |
| WO | WO 2005/054832 | 6/2005 |
| WO | WO 2006/004558 | 1/2006 |
| WO | WO 2006/032844 | 3/2006 |
| WO | WO 2006/059084 | 6/2006 |

OTHER PUBLICATIONS

Nykypanchuk, "Brownian Motion of DNA Confined Within a Two-Dimensional Array," *Science*, Aug. 9, 2002, pp. 987-990, vol. 297, www.sciencemag.org.

Ertaz, "Lateral Separation of Macromolecules and Polyelectrolytes in Microlithographic Arrays ," *Physical Review Letters*, Feb. 16, 1998, pp. 1552-1555, vol. 80, The American Physical Society.

Chou, et al., "Electrodeless Dielectrophoresis of Single- and Double-Stranded DNA," *Biophysical Journal*, Oct. 2002, pp. 217-2179, vol. 83.

Korda, et al., "Kinetically Locked-In Colloidal Transport in an Array of Optical Tweezers," *Physical Review Letters*, Sep. 16, 2002, Article No. 128301, vol. 89, No. 12.

MacDonald, et al. "Microfluidic Sorting in an Optical Lattice," *Letters to Nature*, Nov. 27, 2003, pp. 421-424, vol. 426, Nature Publishing Group.

Sancho, et al, "Reply" *Physical Review Letters*, May 12, 2005, Article 188902, vol. 94, The American Physical Society.

Paterson, et al., "Light-induced Cell Separation in a Tailored Optical Landscape," *Applied Physics Letters*, Sep. 13, 2005, Article 123901, vol. 87.

Duke, et al., "Microfabricated Sieve for the Continuous Sorting of Macromolecules," *Physical Review Letters*, Feb. 16, 1998, pp. 1552-1555, vol. 80.

International Search Reported dated Apr. 23, 2008, Application No. PCT/GB2007/003578, filed Sep. 20, 2007.

M.P. Macdonald, G.C. Spalding and K. Dholakia; *Microfluidic Sorting in an Optical Lattice*; Nature, Nov. 27, 2003; pp. 421-424; vol. 426; 2003 Nature Publishing Group (XP-002289740).

Jennifer E. Curtis, Brian A. Koss and David G. Grier; *Dynamic Holographic Optical Tweezers*; Optics Communications; Jun. 15, 2002; pp. 169-175; vol. 207; 2002 Elsevier Science B.V.

Eric R. Dufresne and David G. Grier; *Optical Tweezer Arrays and Optical Substrates Created with Diffractive Optics*; Review of Scientific Instruments; May 5, 1998; pp. 1974-1977; vol. 69, No. 5; 1998 American Institute of Physics.

J. Han and H.G. Craighead; *Separation of Long DNA Molecules in a Microfabricated Entropic Trap Array*; Science; 12 May 2000; pp. 1026- 1029; vol. 288.

Dmytro Nykypanchuk, Helmut H. Strey and David A. Hoagland; *Brownian Motion of DNA Confined Within a Two-Dimensional Array*; Science; Aug. 9, 2002; pp. 987-990; vol. 297.

Deniz Ertas; *Lateral Separation of Macromolecules and Polyelectrolytes in Microlithographic Arrays*; Physical Review Letters; Feb. 16, 1998; pp. 1548-1551; vol. 80, No. 7; 1998 The American Physical Society.

T.A.J. Duke and R.H. Austin; *Microfabricated Sieve for the Continuous Sorting of Macromolecules*; Physical Review Letters; Feb. 16, 1998; pp. 1552-1555; vol. 80, No. 7; 1998 The American Physical Society.

Chia-Fu Chou, Jonas O. Tegenfeldt, Olgica Bakajin, Shirley S. Chan, Edward C. Cox, Nicholas Darnton, Thomas Duke and Robert H. Austin; *Electrodeless Dielectrophoresis of Single- and Double-Stranded DNA*; Biophysical Journal; Oct. 2002; pp. 2170-2179; vol. 83; 2002 Biophysical Society.

Pamela T. Korda, Michael B. Taylor and David G. Grier; *Kinetically Locked-In Colloidal Transport in an Array of Optical Tweezers*; Physical Review Letters; Sep. 16, 2002; pp. 128301-1-128301-4; vol. 89, No. 12; 2002 The American Physical Society.

International Search Report for PCT/GB2004/001993 completed Jul. 23, 2004.

Office Action dated Apr. 27, 2009, Canadian Application No. 2,524,646.

Office Action dated Feb. 8, 2010, Canadian Application No. 2,524,646.

Office Action dated Nov. 5, 2008, U.S. Appl. No. 10/554,937.

Office Action dated May 5, 2009, U.S. Appl. No. 10/554,937.

Office Action dated Feb. 17, 2011, U.S. Appl. No. 10/554,937.

Office Action dated Jun. 16, 2011, U.S. Appl. No. 10/554,937.

Office Action dated Nov. 30, 2011, U.S. Appl. No. 10/554,937.

Office Action dated Sep. 13, 2012, U.S. Appl. No. 10/554,937 English Language Translation.

Applicant's Amendment to U.S. Appl. No. 10/554,937, dated Feb. 13, 2013 in Response to a Non-Final Office Action dated S ep. 13, 2012, 9 pages.

Padgett, et al.; "The Angular Momentum of Light: Optical Spanners and the Rotational Frequency Shift," *Optical and Quantum Electronics*, pp. 1-12, vol. 31, No. 1, Chapman and Hall, London, Great Britain.

Padgett, et al.; "Optical Tweezers and Spanners," *Physics World*, Sep. 1997, pp.35-38, IOP Publishing, Bristol Great Britain.

Ramser, et al.; "A Microfluidic System Enabling Raman Measurements of the Oxygenation Cycle in Single Optically Trapped Red Blood Cells," *Lab on a Chip*, Feb. 21, 2005, pp. 431-436, No. 5, Royal Society of Chemistry, Cambridge, Great Britain.

International Search Reported dated Jul. 1, 2008, for application PCT/GB2007/003573, filed Dec. 20, 2007.

Office Action dated Dec. 6, 2012, U.S. Appl. No. 12/442,327.

Dharmadhikari, et al..; "Torque-generating malaria-infected Red Blood Cells in an Optical Trap,", Mar. 22, 2004, vol. 12, No. 6/Optics Express 1179-1184.

* cited by examiner

ACOUSTO-OPTIC SORTING

The present invention relates to optical sorting or separation of particles, and in particular cells.

BACKGROUND OF THE INVENTION

Many particle sorting or separation schemes exist, ranging from gel-electrophoresis, capillary electrophoresis, and analytical centrifuging to novel, entropic barriers. Examples of these are described by J. Han, H. G. Craighead, Science 288, 1026-1029 (May 12, 2000) and D. Nykypanchuk, H. H. Strey, D. A. Hoagland, Science 297, 987-990 (Aug. 9, 2002), the contents of which are incorporated herein by reference. The majority of these known techniques separate a polydisperse mixture in a flowing fluid into bands containing particles that travel at different velocities along the direction of flow. This typically leads to batch processing. In electrophoresis a gel is used to obtain a size-dependent mobility. Recovery of fractions is achieved through post-processing of the gel. However, despite its widespread use and effectiveness this methodology is slow and importantly, due to limited pore sizes, has difficulty in separating objects at the microscopic size level, for example cells, chromosomes, and colloidal matter.

Lithographically fabricated two-dimensional, asymmetric artificial gels are also used. Examples of these are described in the articles by D. Ertas, Physical Review Letters 80, 1548-1551 (Feb. 16, 1998); T. A. I Duke, R. H. Austin, Physical Review Letters 80, 1552-1555 (Feb. 16, 1998) and C. F. Chou et al., Biophysical Journal 83, 2170-2179 (October 2002), the contents of which are incorporated herein by reference. These gels yield separation transverse to the direction of flow. Because of this, they can be operated in a continuous fashion, with various fractions taken up by separate collection channels. However, sorting based on diffusion becomes impractically slow at the microscopic scale and above.

Recent years have witnessed a major growth in the exploration of particle motion on optical landscapes. An example of this is described in the article "Kinetically Locked-in Colloidal Transport in an Array of Optical Tweezers" by P. T. Korda et al, Physical Review Letters 89, Number 12, Art. No. 128301 (16 Sep. 2002), the contents of which are incorporated herein by reference. In this case, a monolayer of colloidal spheres is allowed to flow through an array of discrete optical traps. By varying the orientation of the trap lattice it was shown that the direction of flow of the spheres could be varied. Because of this, it was suggested that the lattice could be used to continuously fractionate mesoscopic particles. However, because of the use of a lattice of localized discrete traps, the observed kinetically locked-in channelling along low-index lattice vectors was intrinsically limited to small-angle deflections. In practice, this limits the practicality of the lattice for use in sorting.

PCT/GB2004/001993, the contents of which are incorporated herein by reference, describes yet another optical sorting scheme. In this, three-dimensional optical lattices are used for sorting and fractionation of biological and colloidal material in a microfluidic flow. Different particles follow different trajectories across the landscape and consequently exit at different points. The selectivity and basis of this form of sorting is the affinity of a given particle to the features of the optical landscape. This is also described by M. MacDonald, G. Spalding and K. Dholakia, in Nature 426, 421 (2003), and by A. M. Lacasta, et al., in Physical Review Letters (2005), 94, 188902, the contents of which are incorporated herein by reference. Even in the absence of fluid flow periodic optical patterns may be used for sorting, see L. Paterson, et al., Applied Physics Letters (2005), 87, 123901, the contents of which are incorporated herein by reference.

To date optical sorting has been done using holographic and interferometric methods. Both of these have drawbacks. Interferometric systems require specialist beam splitting components and are not reconfigurable. Spatial light modulators and holographic techniques offer the possibility of changing light patterns but are of relatively poor beam quality and efficiency. Also, spatial light modulators and many holograms cannot handle high laser powers, and complex algorithms are required for good quality 3D light patterns. They also have very slow refresh rates, which limits their use in dynamic environments. Both have limitations in the force that can be applied to micro-particles, because the temporal variation of the light field cannot be readily used to enhance the optical separation.

SUMMARY OF THE INVENTION

According to one aspect of the present invention, there is provided a method for sorting particles in a fluid comprising generating an optical landscape using an acousto-optic device. The optical landscape may take any desired form. For example, the optical landscape may have a potential that varies, for example gradually in a pre-determined direction or dimension.

By using an acousto-optic device, the optical landscape may be very rapidly switched in time, which means that the optical sorting can be easily re-configured for different applications. This has significant practical advantages for example for lab on chip applications.

Acousto-optic devices allow the power, frequency or spatial direction of a laser beam to be controlled with an electrical drive signal using the acousto-optic effect, i.e., the modification of the refractive index by the oscillating mechanical pressure of a sound wave. The key element of an acousto-optic device is a transparent crystal or piece of glass through which light propagates. Attached to the crystal is a piezoelectric transducer that is used to excite a high-frequency sound wave, typically with a frequency of the order of 100 MHz.

Light passing through an acousto-optic crystal experiences Bragg diffraction at the periodic refractive index grating generated by the sound wave. The optical scattered beam has a slightly modified optical frequency and a slightly different direction. The frequency and direction of the scattered beam can be controlled via the frequency of the sound wave, while the acoustic power allows the optical power to be rapidly controlled. For sufficiently high acoustic power, more than 50% of the optical power can be diffracted in one axis. The rapid refresh rate of this system means that its use in optical sorting allows the optical landscape to be rapidly and dynamically reconfigured, even at relatively high powers.

Sorting the particles may involve physically separating them into different regions or subjecting the particles to an optical process that only one type is sensitive to. In the latter case, where a mixture of cells is being sorted, it may be subjected to an optical process that preferentially kills or de-activates or destroys one type of cell, so that the output is a sample that is enriched with one or more other types of cell. For example the method may be for sorting white and red cells and may involve using an optical field to cause the red cells to flip, thereby causing the red cells to lyse. The optical field may comprise an optical funnel. One or two lines of light may be used to define the optical funnel.

Preferably, the optical landscape has a potential that varies. The optical landscape may have a potential that varies gradually in a pre-determined direction or dimension. Alternatively or additionally, the optical landscape may create a potential that varies discontinuously or in steps. The optical landscape may have an optical funnel for directing particles into the optical sorting landscape.

In a preferred embodiment, the fluid in which the particles are suspended may be caused to flow. In this case, the optical landscape or pattern may have a gradient force that acts with or against the fluid flow. When opposing the flow, the sorting occurs due to the selective balance between each of the species being sorted, the balance occurring at different values of power and/or flow due to the differing physical properties of each species of the sample.

According to another aspect of the present invention, there is provided a system for sorting particles comprising means for generating a light pattern and/or optical landscape using an acousto-optic device. Preferably, the system includes means for causing the fluid to flow during sorting.

According to yet another aspect of the present invention, there is provided an optical sorting system for sorting particles, for example cells, the system being arranged to provide an optical landscape having a first region for focussing or directing particles into a second region that is arranged to sort the particles.

Preferably, the first region acts as an optical funnel. The first region may have a substantially constant optical potential.

Preferably, the second region has a potential that varies. The second region may have a potential that varies in a pre-determined direction or dimension. Alternatively or additionally, the second region may have a potential that varies discontinuously or in steps. The potential landscape may have one or more exit ports to provide an exit for sorted particles. The exit ports may be sized to accommodate specific sized particles. The exit ports may be positioned at junctions between different sorting regions, that is sorting regions associated with different particles. The second region may have an optical potential that is non-periodic.

According to still another aspect of the invention, there is provided an optical system for sorting particles, for example cells, the system being arranged to provide a non-periodic sorting potential landscape.

The potential landscape may vary in at least one dimension. The potential landscape may vary gradually over a pre-determined area.

The potential landscape may have one or more exit ports to provide an exit for sorted particles. The exit ports may be sized to accommodate specific sized particles. The exit ports may be positioned at junctions between different sorting regions, that is sorting regions associated with different particles.

According to a still further aspect of the invention, there is provided an optical system arranged to provide an optical landscape, the landscape being such as to preferentially deactivate or damage or lyse one type of cell, for example a red cell, in a fluid containing a mixture of cells, for example both red and white cells.

BRIEF DESCRIPTION OF THE DRAWINGS

Various aspects of the invention will now be described by way of example only and with reference to the accompanying drawings, of which.

DETAILED DESCRIPTION OF THE DRAWINGS

The invention provides particle sorting in a fluid using an optical landscape generated by an acousto-optic device. The optical landscape may take any desired form. For example, the optical landscape may have a potential that varies gradually in a pre-determined direction or dimension. To create the optical landscape an optical trapping or tweezing arrangement can be used, in which light is generated by an acousto-optic device.

Figure 1:
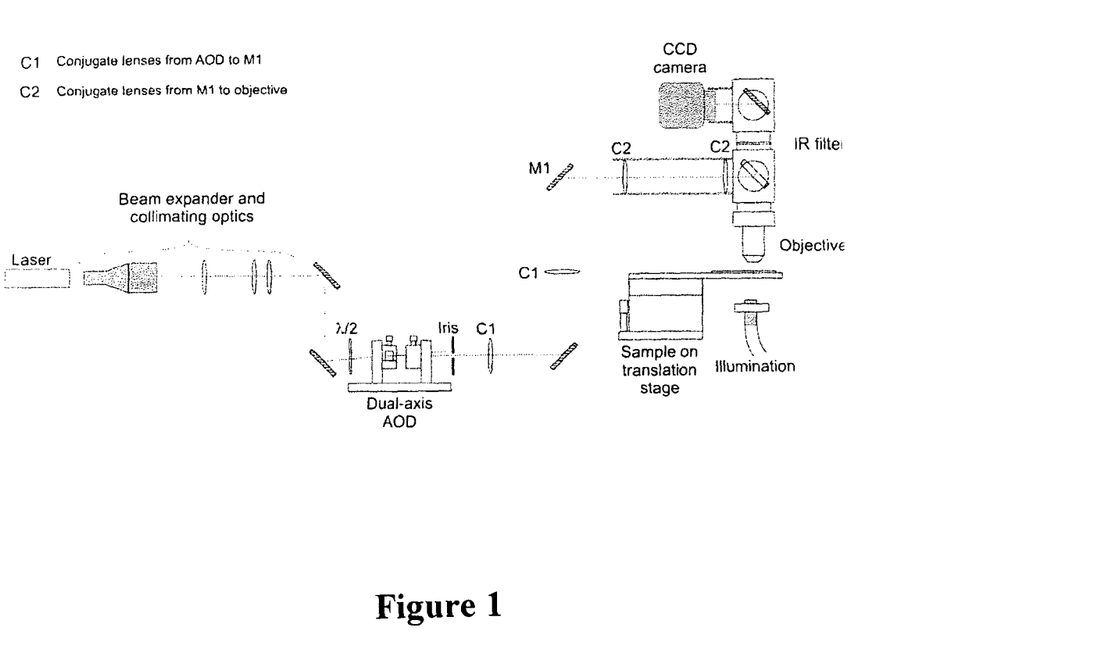
FIG. 1 is a block diagram of an optical system for generating an optical landscape for sorting particles.

FIG. 1 shows the layout of a typical optical trapping or tweezing system that can be used in accordance with the present invention. This has a laser with a beam expander and collimating optics at its output. Light output from the collimating optics is directed onto a dual axis acousto-optic system, for example the system provided by NEOS, USA or Inter-action, USA. This has two acousto-optic crystals back-to-back or in one unit to permit translation in the beam in both the x and y directions.

The dual-axis system is operable to produce an optical beam and raster scan it in both the x and y dimension. The beam scan is controlled using a LabVIEW program and two variable DC voltages generated by a National Instruments DAQ card (MI0-16E-4). The program takes as an input a standard 256-level grayscale bitmap representation of the desired optical distribution. The 2D image is then processed into two waveforms that are fed to the DAQ card. These waveforms contain the positional information for the x and y components of the acousto-optic device respectively.

The acousto-optic system is placed at a point conjugate to the back aperture of a 100×NA=1.25 oil immersion microscope objective. Light from the acousto-optic system passes through conjugate lenses C1 and conjugate lenses C2 and onto the objective lens of the microscope, where it is directed towards a sample stage. A CCD camera is provided to capture images of the optical landscape and the sample.

To create optical landscapes for particle sorting, a 1070 nm yttrium fibre laser (IPG Laser) was used with an output beam of diameter 5 mm and bandwidth of 5 GHz. The power in the beam after the acousto-optic device was measured to be of the order of 400 mW, although 100 mW would be sufficient. The acousto-optic device was caused to scan out the desired optical landscape as defined by the LabVIEW program. Observations of the colloid dynamics and light scattering were performed through the same objective as for trapping and sorting and white light illumination was employed from below using a high power white light source. Particle trajectories were determined over a region of the created landscape. Particles were tracked at standard video frame rates (25 frames/sec) and trajectories were mapped with LabView™ software using a pattern-matching algorithm.

For sorting, the optical landscape has to vary in at least one direction. In experiments to test the effectiveness of the acousto-optic device, multiple grayscale levels were defined in a raster-scanned laser image, each level having a different optical potential. To achieve this, the laser was paused at each 'pixel' for a varying amount of time. The length of the pause was determined by the brightness of the corresponding pixel in the original input image. The rate at which the image is repeated can be selected by the user. For the experiments described hereinafter the images were scanned at 100 Hz. The spatial scaling of the image in the sample plane was chosen so that the displacement of adjacent pixels was smaller than the diameter of the scanning beam (2.5 µm). This enabled the generation of an effectively continuous time-integrated optical landscape rather than an array of discrete trapping sites.

An important consideration is a temporal effect due to the action of the raster scan on the particle. High-index particles were observed to move along the direction of the scan. In a 2D raster scan, particles moved along a diagonal in the plane of the applied image. In general, particle drift due to this scanning effect may dominate the behavior generated by the local intensity gradient of the applied pattern. To study particle behavior free from such time varying effects, this scanning artifact can be removed. For example, since the temporal effect arises due to the sequential and directional nature of the raster scan, one option is to randomize the order in which the pixels are drawn out by the laser. Another option is to apply small sequential changes to the AOD driver signal. This can be achieved by running the raster scan in reverse every second frame. This process was observed to suppress particle behaviour associated with the scanning, so that particle behaviour due to the applied time-integrated optical landscape could be studied.

Figure 2A:
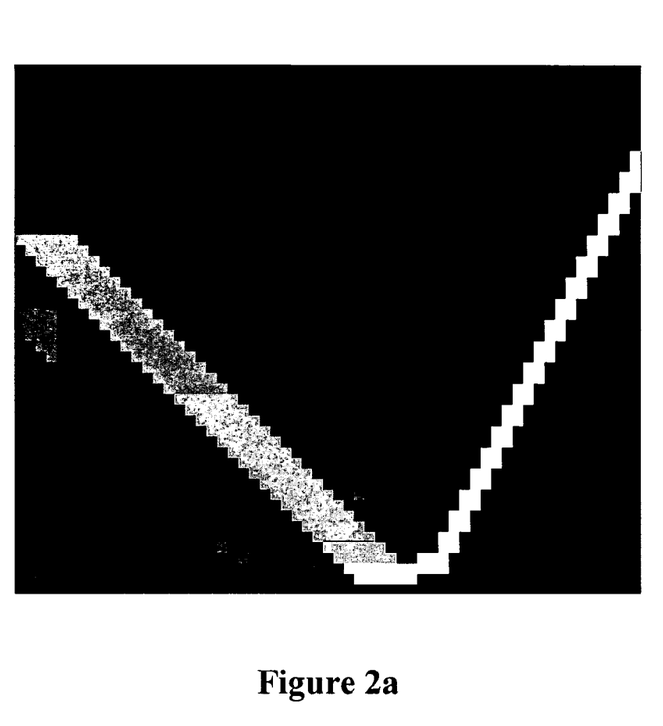
FIG. 2(a) is an image of an optical landscape that was used to sort three different size particles.
Figure 2B:
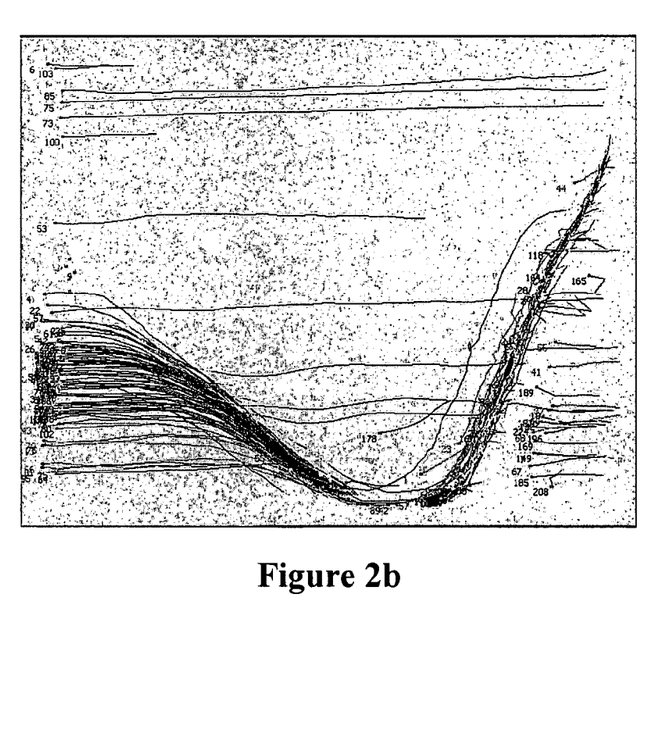
FIG. 2(b) shows particles tracked within the landscape of FIG. 2(a)

FIG. 2 shows a scanned optical pattern for sorting a polydisperse mixture of silica spheres suspended in de-ionized water, the spheres having three different sizes: 2.47 µm, 3.01 µm and 5.08 µm. The landscape has a uniform bright diagonal line to the right of the pattern which acts as an optical funnel for channelling the poly-disperse colloidal mixture into a near uniform single or dual particle stream approximately 2 µm in width. To the left of the optical funnel is an exit ramp consisting of a line feature of varying intensity. This guides the particle stream across the flow. This has a non-periodic, graded optical intensity with distinct zones of decreasing intensity along its length. The lack of periodicity permits different sized/refractive index objects to exit the light pattern at different points. Fluid flow may be varied typically at velocities from 0-100 µm/s from right to left in FIG. 2. While traversing the exit ramp, the spheres experience a hydrodynamic drag force pulling them to the left. To a reasonable approximation, this force scales linearly with the particle radius. In the pattern, the spheres experience an optical trapping force that scales as the cube of the particle radius. As a result, smaller particles are likely to be drawn out of the optical landscape first.

FIG. 2 shows the sorting results achieved using the funnel and exit ramp optical landscape. When the particle stream from the optical funnel was incident upon the graded intensity line each particle interacted differently with the optical potential. Subsequently each sphere moved along the graded line to a different extent depending on its size and exited the line at different point. FIG. 2 shows tracked trajectories for the three particles showing the particle behaviour. Calculations verify that objects can also be sorted based on refractive index in a similar manner. In the optical field of FIG. 2, the smallest particles (2.47 µm) exit first, while larger particles continue further along the ramp.

Figure 3A:
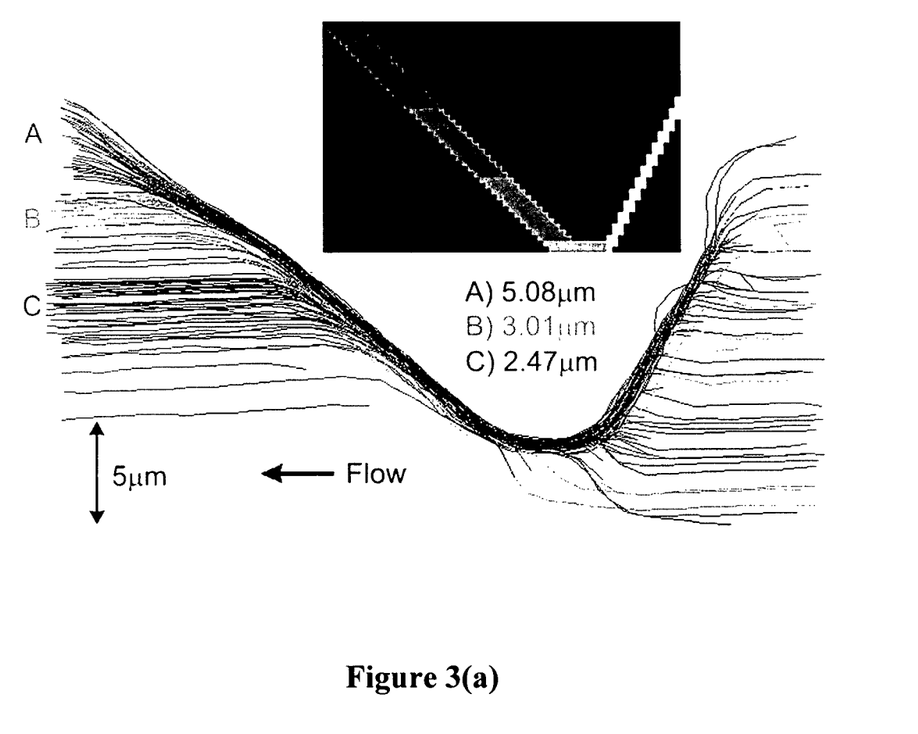
FIG. 3(a) is an image of another optical landscape that was used to sort four different size particles but without any discreteness (i.e. gaps) along the exit path of the landscape.
Figure 3B:
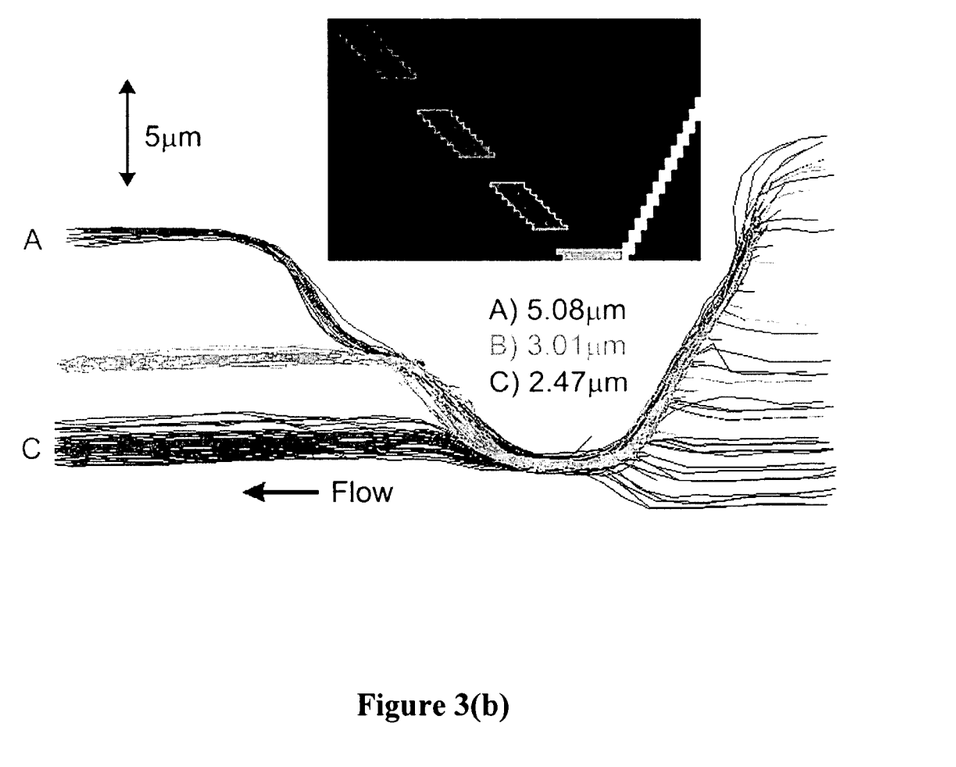
FIG. 3(b) is an image of an optical landscape (inset) that was used to sort three different size particles into separated parallel laminar flows with discrete gaps in the exit path, with trajectories of the trapped particles are shown.

To improve the definition of where particles exit the ramp, discrete gaps of increasing size were inserted between the regions of constant intensity. The size of each exit port is selected to accommodate the size of the particles at the relevant level of intensity. As shown each port is positioned at a junction between different particle sorting regions. Having these ports produced highly localized particle exit streams, as shown in FIG. 3. If particle-particle collisions and interactions are avoided, which can be achieved by keeping the density of particles sufficiently low, near-100% sorting efficiency can be achieved.

Figure 4:
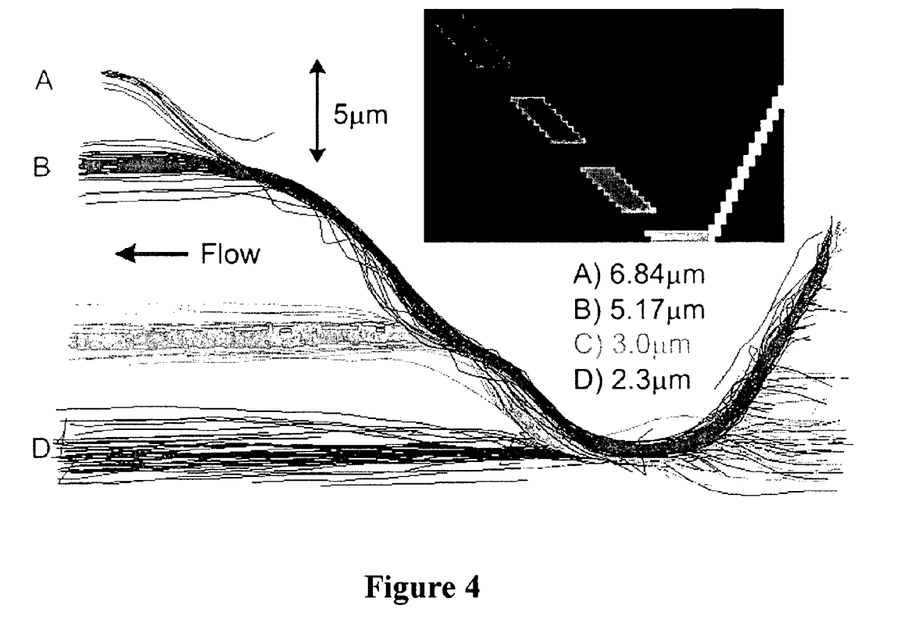
FIG. 4 is an image of an optical landscape (inset) that was used to sort four different size particles into separated parallel laminar flows with discrete gaps in the exit path, with trajectories of the trapped particles shown.

FIG. 4 shows more results obtained using the same optical pattern as that of FIG. 3, but in this case for a mixture containing four different sizes of silica microspheres, these being 2.3 µm, 3.0 µm, 5.17 µm and 6.84 µm. Again, if particle-particle collisions and interactions are avoided, which can be achieved by keeping the density of particles sufficiently low, near-100% sorting efficiency can be achieved.

In the above examples, the temporal effects of the scan rate were removed and particles sorted by the exit ramp were moved away from it by the flow of fluid in the sample chamber. However, the scanning direction may be used to enhance the sorting characteristics. For example, if the laser beam is caused to counter-propagate against the flow, the force on particles is enhanced, so that the sensitivity of the sorting is increased. In some circumstances, tuning the scan rate of the acousto-optic system allows particles to be sorted, even in the absence of fluid flow. For example, the scan rate could be tuned so that large particles are trapped and dragged out of the flow within the sorting landscape, whereas smaller objects may be permitted to diffuse away. In this case, the scanning rate of the device must exceed the particle diffusion time of particles due to Brownian motion. The effectiveness of this is shown in FIG. 5.

Figure 5:
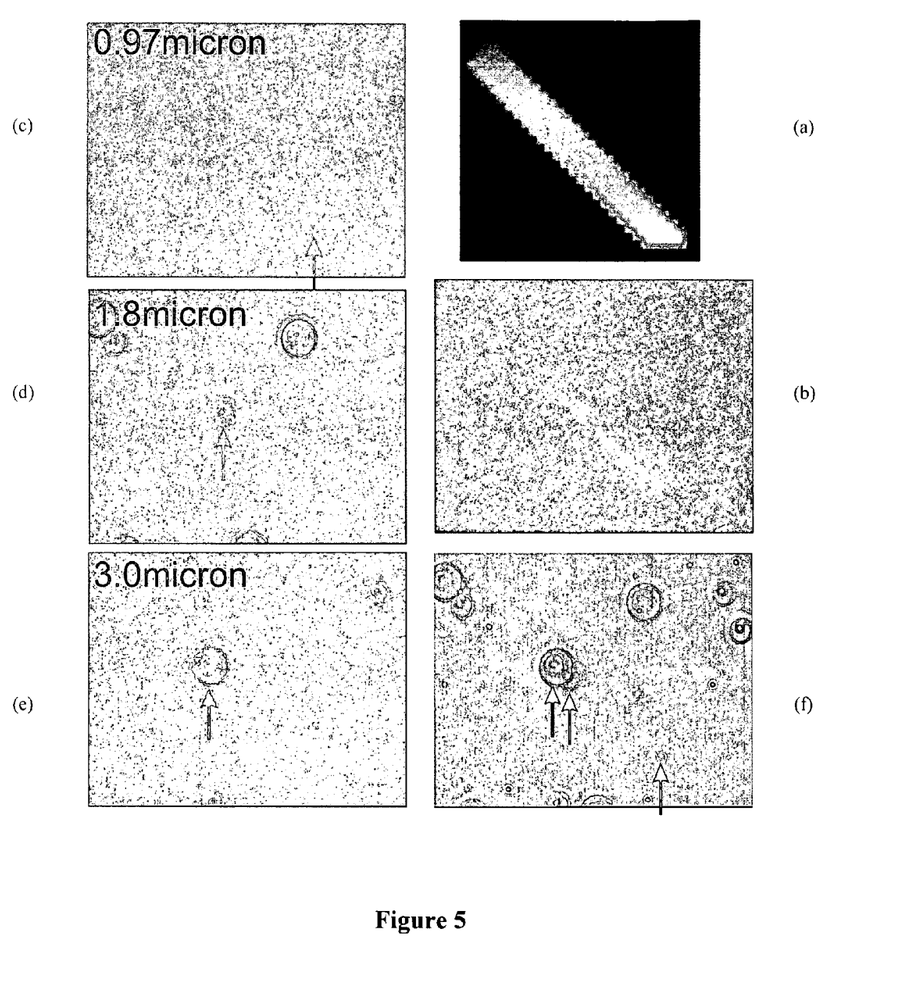
FIG. 5(a) is a bit map/design of a pattern for scanning an acousto-optic device under computer control.
FIG. 5(b) is an image of the light pattern of FIG. 5(a) created using an acousto-optic device.
FIG. 5(c) shows the position of a small particle in the landscape of FIG. 5(b)
FIG. 5(d) shows the position of a medium sized particle in the landscape of FIG. 5(b)
FIG. 5(e) shows the position of a large particle in the landscape of FIG. 5(b)
FIG. 5(f) is a superposition of FIGS. 5(c) to (e)

FIG. 5 shows how the time varying capability of a scanned optical landscape can be used to generate a scanned version of optical chromatography. A rectangular sample chamber containing a mixture of particles having different sizes was scanned from left to right and then upwards in a sample with no flow. FIG. 5(a) shows a bit map/design of the pattern for the acousto-optic device to define. FIG. 5(b) shows an image of a light pattern created. FIGS. 5(c) to (d) show the positions of small, medium sized and large particles in the landscape of FIG. 5(b). FIG. 5(f) is a superposition of FIGS. 5(c) to (e). From this it can be seen that particles respond differently and thus take up different lateral positions. This happens in only a few seconds. Hence with or without fluid flow in the sample chamber, the present invention can be used to provide effective particle sorting.

Figure 6:
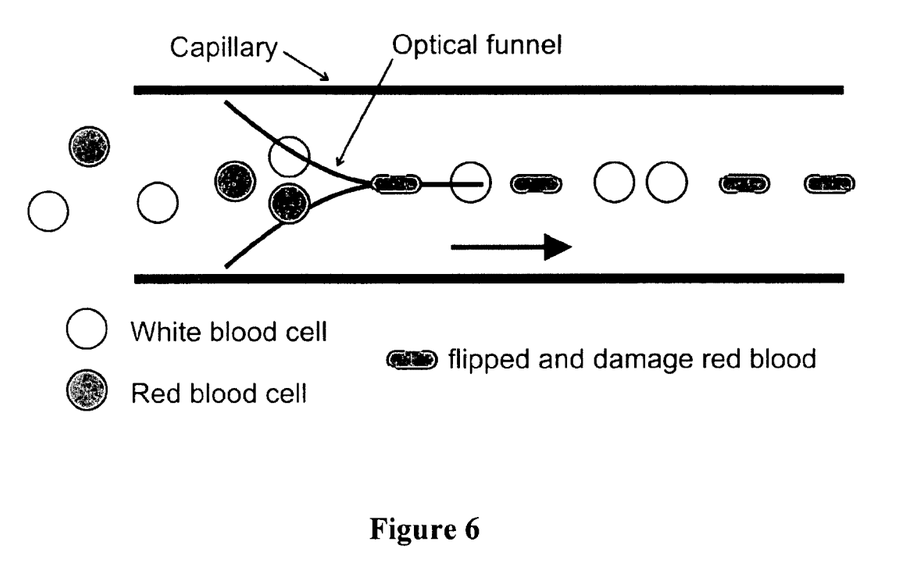
FIG. 6 shows an alternative cell sorting arrangement.

FIG. 6 shows another optical landscape for sorting cells. Preferably, this landscape is generated using an acousto-optic device, as described above. The optical landscape works by subjecting the cells to an optical field that only one type is sensitive to. In this case, the landscape is an optical funnel that focuses down a broad flow of particles into a single or dual file flow of particles. The particle mix is subjected to an acousto-optically generated field that damages or otherwise de-activates one type of cell, so that it ceases or is unable to fulfil its biological function. The result is that the output is a sample that is enriched with one or more other types of cell.

Advantageously, the optical landscape of FIG. 6 can be used for sorting red cells from white cells. Red cells are biconcave discs and white cells are generally spherical. In this case, the cells are in a fluid flow and the optical landscape is funnel shaped, with the funnel narrowing in the direction of fluid flow. As shown, two converging beams of light create the funnel, although other arrangements may be used. A fluid containing a mixture of red and white cells is introduced into the optical field and caused to flow towards the narrow end of the funnel. The flow of white cells is focussed down by the funnel but otherwise passes through unaffected. In contrast, the red cells flip to align with the narrow output of the optical funnel and become lysed due mechanical stresses induced in the flipping process, so that only active white cells make it through. In this way, the output is enriched with white cells.

The present invention allows sorting of a polydisperse mixture of particles in an optical potential landscape created using a dual-axis acousto-optic modulator. The use of a reconfigurable device such as an acousto-optic device allows fast and easy modification of the landscape. The inclusion of tailored gaps in the exit ramp leads to highly localized parallel laminar exit streams for different particle sizes.

Because the pattern and hence the functionality of the device in which the invention is embodied can be changed in real time, this opens the possibility of feeding back information into the system and dynamically changing the optical landscape in response to that feedback, thereby implying system intelligence. For example a sample can be loaded onto a chip for analysis and the particles sorted. Then, depending on the initial sorting results, the chip can be told to reconfigure itself to perform a new task. Thus an intelligent assay system is provided that might be programmed via a form of pseudo-code. A specific example might be: cells in; enrich for one species of cell; re-circulate to a re-configured optical sorter that sorts for certain sub-species of cells; if sorted analyte produces mostly species A then perform task 1 for further analysis; if it produces mostly B then perform task 2; on result of task 1 or task 2 decide to perform further enrichment/sorting process or remove to extraction chamber. Then a diagnosis can be made or the cells are ready for further work.

A skilled person will appreciate that variations of the disclosed arrangements are possible without departing from the invention. For example, whilst the intensity of the optical landscape at each pixel is described as being determined by the time the laser beam is paused, intensity levels could in principle be controlled by the inclusion of a high-speed amplitude modulator such as a Pockels cell in the optical train, programmed to work in synchronization with the acousto-optic device. Alternatively, an acousto-optic device that can modulate transmitted beam power could be used. Also, whilst the invention has been described primarily with reference to sorting according to particle size, it could equally be used to sort according to the refractive index or shape of the particles. Accordingly the above description of the specific embodiment is made by way of example only and not for the purposes of limitation. It will be clear to the skilled person that minor modifications may be made without significant changes to the operation described.

The invention claimed is:

1. A method for sorting particles in a fluid comprising:
generating an optical landscape; and
flowing the fluid through the optical landscape,
wherein the optical landscape comprises a line feature that has a graded optical intensity that guides particles across the fluid flow and allows different particles to exit the line feature at different positions, thereby sorting the particles in the fluid flow and wherein the graded optical intensity varies discontinuously or in steps.

2. The method as claimed in claim 1 wherein the optical landscape is arranged to sort particles based on size or refractive index or shape.

3. The method as claimed in claim 1 wherein the graded optical intensity varies gradually in a pre-determined direction or dimension.

4. The method of claim 1, wherein the step of generating an optical landscape comprises generating an optical landscape using an acousto-optic device.

5. A method for sorting particles in a fluid comprising:
generating an optical landscape; and
flowing the fluid through the optical landscape,
wherein the optical landscape comprises a line feature that has a graded optical intensity that guides particles across the fluid flow and allows different particles to exit the line feature at different positions, thereby sorting the particles in the fluid flow and wherein at least one gap is formed in the optical landscape, thereby to provide one or more exit ports for sorted particles.

6. The method of claim 5, wherein the step of generating an optical landscape comprises generating an optical landscape using an acousto-optic device.

7. A method for sorting particles in a fluid comprising:
generating an optical landscape; and
flowing the fluid through the optical landscape,
wherein the optical landscape comprises a line feature that has a graded optical intensity that guides particles across the fluid flow and allows different particles to exit the line feature at different positions, thereby sorting the particles in the fluid flow and wherein at least one gap is formed in the optical landscape, thereby to provide one or more exit ports for sorted particles and the exit ports vary in size, thereby to accommodate different size or refractive index or shape of particles.

8. The method of claim 7, wherein the step of generating an optical landscape comprises generating an optical landscape using an acousto-optic device.

9. A method for sorting particles in a fluid comprising:
generating an optical landscape; and
flowing the fluid through the optical landscape,
wherein the optical landscape comprises a line feature that has a graded optical intensity that guides particles across the fluid flow and allows different particles to exit the line feature at different positions, thereby sorting the particles in the fluid flow and wherein an optical funnel is provided and wherein the optical landscape comprises an exit ramp consisting of a line feature that has a graded optical intensity and is provided at an output of the funnel.

10. The method as claimed in claim 9 wherein the optical funnel is sized to provide a single or dual particle stream.

11. The method of claim 9, wherein the step of generating an optical landscape comprises generating an optical landscape using an acousto-optic device.

12. A method for sorting particles in a fluid comprising:
generating an optical landscape;
flowing the fluid through the optical landscape,
wherein the optical landscape comprises a line feature that has a graded optical intensity that guides particles across the fluid flow and allows different particles to exit the line feature at different positions, thereby sorting the particles in the fluid flow; and selecting a scan rate to move particles across the optical sorting landscape.

13. The method of claim 12, wherein the step of generating an optical landscape comprises generating an optical landscape using an acousto-optic device.

14. A system for sorting particles in a fluid comprising:
a first device configured to generate an optical landscape comprising a line feature that has a graded optical intensity that guides particles across the fluid flow and allows different particles to exit the line feature at different positions, thereby sorting the particles in the fluid flow and wherein the graded optical intensity landscape varies discontinuously or in steps; and
a second device causing the fluid to flow during sorting.

15. The system as claimed in claim 9 wherein the optical landscape is arranged to sort particles based on size or refractive index or shape.

16. The system as claimed in claim 9 wherein the graded optical intensity landscape varies gradually in a pre-determined direction or dimension.

17. The system of claim 14, wherein the first device is an acousto-optic device.

18. A system for sorting particles in a fluid comprising:
a first device configured to generate an optical landscape comprising a line feature that has a graded optical intensity that guides particles across the fluid flow and allows different particles to exit the line feature at different positions, thereby sorting the particles in the fluid flow and wherein at least one gap is formed in the optical landscape, thereby to provide one or more exit ports for sorted particles; and
a second device causing the fluid to flow during sorting.

19. The system of claim 18, wherein the first device is an acousto-optic device.

20. A system for sorting particles in a fluid comprising:
a first device configured to generate an optical landscape comprising a line feature that has a graded optical intensity that guides particles across the fluid flow and allows different particles to exit the line feature at different positions, thereby sorting the particles in the fluid flow and wherein at least one gap is formed in the optical landscape, thereby to provide one or more exit ports for sorted particles and the exit ports vary in size, thereby to accommodate different size or refractive index or shape of particles; and
a second device causing the fluid to flow during sorting.

21. The system of claim 20, wherein the first device is an acousto-optic device.

22. A system for sorting particles in a fluid comprising:
a first device configured to generate an optical landscape comprising a line feature that has a graded optical intensity that guides particles across the fluid flow and allows different particles to exit the line feature at different positions, thereby sorting the particles in the fluid flow, wherein an optical funnel is provided for directing particles and wherein the optical landscape comprises an exit ramp consisting of a line feature that has a graded optical intensity and is provided at an output of the funnel; and
a second device causing the fluid to flow during sorting.

23. The system as claimed in claim 14 wherein the optical funnel is sized to provide a single or dual particle stream.

24. The system of claim 22, wherein the first device is an acousto-optic device.

25. A system for sorting particles in a fluid comprising:
a first device configured to generate an optical landscape comprises a line feature that has a graded optical intensity that guides particles across the fluid flow and allows different particles to exit the line feature at different positions, thereby sorting the particles in the fluid flow and wherein the scan rate is selected to move particles across the optical sorting landscape; and
a second device causing the fluid to flow during sorting.

26. The system of claim 25, wherein the first device is an acousto-optic device.

* * * * *